United States Patent [19]
Inaba et al.

[11] Patent Number: 6,040,434
[45] Date of Patent: Mar. 21, 2000

[54] ALDEHYDE OXIDASE INHIBITORS FOR TREATMENT OF AIDS

[76] Inventors: Tadanobu Inaba, 72 Beaconsfield Avenue, Toronto, Ontario, Canada, M6J 3H9; Shirin Fayz, 80 Adelaide Street East, TH #12, Toronto, Ontario, Canada, M5C 1K9; David John Stewart, Unit 401-3980 Inlet Crescent, North Vancouver, British Columbia, Canada, V7G 29P

[21] Appl. No.: 08/984,478

[22] Filed: Dec. 1, 1997

[51] Int. Cl.$^7$ .............................. A61K 31/70; A61K 9/00; A61K 9/22
[52] U.S. Cl. .............................. 536/23; 424/468; 435/25; 435/184; 435/191; 435/163; 514/50; 514/51; 514/974
[58] Field of Search .............................. 424/468; 514/50, 514/51, 974; 536/23; 435/25, 184, 191, 963

[56] References Cited

U.S. PATENT DOCUMENTS

| | | |
|---|---|---|
| 4,724,232 | 2/1988 | Rideout et al. . |
| 4,833,130 | 5/1989 | Rideout et al. . |
| 5,234,913 | 8/1993 | Furman, Jr, et al. . |

OTHER PUBLICATIONS

Beedham, Christine; "Molybdenum Hydroxylases as Drug–Metabolizing Enzymes", *Metabolism Reviews*, 16 (1&2): 119–156; 1986.

Cretton, Erika M., et al.; "Catabolism of 3'–Azido–3'–deoxythymidine in Hepatocytes and Liver Microsomes, with Evidence of Formation of 3'–Amino–3'–deoxythymidine, a Highly Toxic Catabolite for Human Bone Marrow Cells"; *Molecular Pharm.*, 39: 258–266; 1991.

Eagling, V.A., et al.; "The Metabolism of Zidovudine by Human Liver Microsomes In Vitro: Formation of 3'–Amino–3'–deoxythymidine", *Biochem. Pharmacol.*; 48(2): 267–276; 1994.

Fitzsimmons, Michael E., et al.; "Selective Biotransformation of the Human Immunodeficieny Virus Protease Inhibitor Saquinavir by Human Small–Intestinal Cytochrome P4503A4"; *Drug Metab. and Disp.*; 25: 256–266; 1997.

Kitamura, Shigeyuki, et al.; "Reduction of Tertiary Amine N–Oxides by Liver Preparations: Function of Aldehyde Oxidase as a Major N–Oxide Redctase"; *Biochemical and Biophysical Research Comms.*; 121 (3): 749–754; 1984.

Kumar, Gondi N., et al.; "Cytochrome P450—Mediated Metabolism of the HIV–1 Protease Inhibitor Ritonavir (ABT–538) in Human Liver Microsomes"; *J. Pharmacol. Exp. Ther.*; 277: 423–431; 1996.

McLeod, Gavin X., et al.; "Zidovudine: Five Years Later"; *Annals of Internal Medicine*, 117: 487–501; 1992.

Stagg, M. Patrick, et al.; "Clinical pharmacokinetics of 3'–azido–3'–deoxythymidine (zidovudine) and catabolites with formation of a toxic catabolite, 3'–amino–3'–deoxythymidine"; *Clin. Pharmacol. Ther.*; 51: 668–676; 1992.

Sugihara, Kazumi, et al.; "Involvement of Mammalian Liver Cytosols and Aldehyde Oxidase in Reductive Metabolism of Zonisamide"; *Drug Metab. and Disp.*; 24(2): 199–202; 1996.

Veal, Gareth J., et al., "Metabolism of Zidovudine"; *Gen. Pharmac.*; 26(7): 1469–1475; 1995.

*Primary Examiner*—James O. Wilson
*Assistant Examiner*—Howard Owens
*Attorney, Agent, or Firm*—Townsend and Townsend and Crew LLP

[57] ABSTRACT

A new pathway of metabolism of 3'-azido-3'-deoxythymidine (AZT) to 3'-amino-3'-deoxythymidine (AMT) has been described. This pathway involves the enzyme aldehyde oxidase. Aldehyde oxidase inhibitors may be used to reduce AMT formation during therapy with AZT.

13 Claims, No Drawings

ALDEHYDE OXIDASE INHIBITORS FOR TREATMENT OF AIDS

This invention relates to compounds and pharmaceutical compositions for use in the treatment of AIDS. More particularly, the invention relates to compounds which reduce the toxicity of certain drugs employed for AIDS treatment.

BACKGROUND OF THE INVENTION

In the description which follows, references are made to certain literature citations which are listed at the end of the specification. The contents of these are incorporated herein by reference.

One of the earliest drugs to show great promise as an anti-retroviral drug was the reverse transcriptase inhibitor, 3'-azido-3'-deoxythymidine, also known as zidovudine or AZT. AZT is a potent inhibitor of retroviral replication and has been widely used in the treatment of infection with the human immunodeficiency virus (HIV) or treatment of acquired immune deficiency syndrome (AIDS) caused by that virus.

The major limitation to the use or AZT in these therapies is its side-effect of bone marrow toxicity, resulting in granulocytopenia and anemia. This toxicity is caused mainly by a toxic metabolite of AZT, 3'-amino-3'-deoxythymidine or AMT, which is more toxic to bone marrow cells than AZT and has a longer half-life in the circulation (Cretton et al., 1991; Stagg, 1992). Depending on dosage and disease stage, up to 51% of patients treated with AZT suffer bone marrow toxicity. It would therefore be beneficial to find ways of reducing the production of AMT during AZT therapy.

SUMMARY OF THE INVENTION

The present inventors have demonstrated a new pathway of metabolism whereby the drug 3'-azido-3'-deoxythymidine (AZT), which is used to treat HIV infection and AIDS, is converted to the toxic metabolite 3'-amino-3'-deoxythymidine (AMT). This conversion is effected by the enzyme aldehyde oxidase. Inhibitors of aldehyde oxidase may therefore be used to reduce AMT production from AZT and to provide improved therapeutic regimes for AIDS and HIV victims.

DETAILED DESCRIPTION OF THE INVENTION

AZT is metabolised and eliminated from the body by three pathways (Veal et al., 1995). The predominant pathway of metabolism is by glucuronide formation and renal excretion. A minor amount of AZT is phosphorylated in lymphocytes and thereby enabled to exert its anti-viral action. The third pathway of metabolism is by reduction of the azido moiety of AZT to give AMT. Eagling (1994) demonstrated the conversion of AZT to AMT by human liver microsomes and concluded that the conversion was mediated by both microsomal cytochrome P450 isozymes and microsomal NADPH-cytochrome P450 reductase.

The present inventors have found that the microsomal pathway is not the major pathway of AZT conversion to AMT and have identified a new pathway which is much more active in AMT production.

Using human liver samples, and measuring conversion of AZT to AMT, the inventors have shown that less than 10% of AMT formation is due to microsomal enzyme activity and that 90% or more of AMT formation is due to the activity of cytosolic aldehyde oxidase.

Aldehyde oxidase (EC 1.2.3.1) is a molybdenum hydroxylase (Beedham, 1985), which has been suggested to play a role in the breakdown of drugs such as the anticonvulsant, zonisamide (Sugihara, 1996). It was not previously suspected to play a role in the breakdown of AZT.

The present invention provides for improved therapy of any disease or condition which is treatable by administration of AZT, including retroviral infections in humans and other mammals, psoriasis and amyotrophic lateral sclerosis.

In accordance with one embodiment, the invention provides a method for treating retroviral infections in humans or other mammals, by administering a combination of AZT and an aldehyde oxidase inhibitor.

In a further embodiment, the invention provides a method for treating Feline Immunodeficiency Virus infections or feline T-lyphotropic lentivirus infections which are treatable with AZT (Hart et al., 1995; Horzinek, 1987).

Retroviruses are also known to infect cattle and birds and these infections also may be treated by the methods of the invention.

In a preferred embodiment, the invention provides a method for treating HIV infection or AIDS in humans by administering a combination of AZT and an aldehyde oxidase inhibitor. The aldehyde oxidase inhibitor is administered in an amount effective to reduce or prevent the conversion of the administered AZT to AMT in the tissues and organs of the human.

Administration of an aldehyde oxidase inhibitor in combination with AZT will permit an increased dose of AZT to be tolerated, thus providing improved treatment of the HIV infection or AIDS.

HIV infections which may be treated by the method of the invention include infections with human immunodeficiency viruses such as HIV-1 and HIV-2 viruses or with human T-cell lymphotropic viruses such as HTLV-1 or HTLV-2. HIV infections may be treated either while the subject is asymptomatic or after the appearance of a disease such as AIDS or an AIDS-related clinical condition.

The aldehyde oxidase inhibitor should be a pharmaceutically acceptable compound. For example, the aldehyde oxidase inhibitor may be pyrazinamide, terfenadine, estradiol, tinidazole, nifedipine, loratadine, folic acid, riboflavin, astemizole, saquinavir, indinavir, thioctic acid, chloramphenicol, clarithromycin, miconazole, ketoconazole, pyridoxal, esculetin, clotrimazole and ritonavir.

AZT can be prepared by conventional synthetic techniques, for example as described in U.S. Pat. No. 4,724,232, which is incorporated herein by reference. AZT can also be obtained commercially, for example from Glaxo Wellcome. AZT may also be administered in the form of pharmaceutically acceptable salts or derivatives, as described in U.S. Pat. No. 4,724,232.

The present invention also provides pharmaceutical compositions of at least one aldehyde oxidase inhibitor and a pharmaceutically acceptable carrier, for administration in combination with AZT.

The invention also provides for the use of a combination of AZT and at least one aldehyde oxidase inhibitor in the manufacture of a medicament for the treatment of HIV infection or AIDS.

The various aldehyde oxidase inhibitors may be synthesised by published methods or may be obtained from commercial drug houses. For example, ketoconazole and miconazole can be obtained from Janssen (Beerse, Belgium)

clotrimazole from Miles or Boehringer Ingelheim (Ridgefield, Connecticut) and clarithromycin can be obtained from Abbott Laboratories (Chicago, Ill.).

Various aldehyde oxidase inhibitors may also be used in the form of pharmaceutically acceptable salts, as is understood by those of ordinary skill in the art. Derivatives such as esters may also provide controlled release preparations of the inhibitors.

The combination of AZT and aldehyde oxidase inhibitor administered may comprise separate administrations of the two components or, preferably, AZT and one or more aldehyde oxidase inhibitors are prepared in a single dosage form.

If AZT and an aldehyde oxidase inhibitor are administered as separate pharmaceutical compositions, the timing and dosage of the aldehyde oxidase inhibitor administration should preferably be adjusted to optimise the reduction or prevention of AZT conversion to AMT.

Preferably, the administered inhibitor should reduce the blood level of AMT, measured as $C_{max}$ or AUC, by at least about 20%.

Preferably, a minimum ratio of inhibitor to AZT must be maintained in the blood or tissues, below which AMT formation is no longer significantly inhibited. A suitable inhibitor/AZT ratio can be arrived at by administering a standard dosage of AZT (for example, in the range 600–1200 mg/day) along with various dosages of inhibitor and measuring AUC. The measurements of AUC should be made at steady state i.e. after administration has been continued for at least 6 half-lives of AZT and the inhibitor.

In a preferred embodiment, the inhibitor has a longer half-life than that of AZT and is administered at the same time as AZT. The fluctuations in the blood levels of the inhibitor will be less extreme than that of the AZT. Provided the inhibitor adequately suppresses AMT formation at $C_{max}$ for AZT, the inhibitor could be taken at the same time as AZT even if absorption were faster or slower than AZT.

If subjects with HIV infection or AIDS are required to take a number of separate medications, especially if these have to be taken at critical time intervals, the burden on an already afflicted subject is increased and compliance is likely to suffer. It is therefore useful if medications can be combined in a single dosage form.

The present invention further provides a combination of AZT and an aldehyde oxidase inhibitor in a single dosage form pharmaceutical composition.

Where AZT and an aldehyde oxidase inhibitor are to be combined in the same dosage form, the proportion of AZT to aldehyde oxidase inhibitor is determined in the same way as when the two drugs are to be administered separately. The dissolution characteristics for the capsule or tablet form should be adjusted, if necessary, such that AZT and the aldehyde oxidase inhibitor are released at the same rate. This should be the situation in an immediate release formulation. Where the inhibitor is affected by food, the timing of administration of the single dosage form should be such that optimal absorption of the inhibitor is obtained i.e., either with or without food as required.

Adjustments can be made to the formulations to compensate for differences in absorption rate and/or elimination rate to maintain an adequate ratio of the two components.

Although AZT and aldehyde oxidase inhibitors are likely to have different half lives in the body, frequency of administration of a single dosage form is set by the component with the shorter half life. Retroviral drugs generally tend to be eliminated rapidly, so frequent dosing is necessary to maintain adequate blood and tissue levels. If larger doses are given at less frequent intervals, the peak and minimum blood levels tend to be much further apart, with the peak levels approaching toxicity and the minimum levels approaching the threshold level. A preferred approach in such situations is to provide a sustained release formation which slowly releases the active component or components and reduces the extreme fluctuations of blood and tissue levels.

Sustained release preparations of AZT have been described, for example, in U.S. Pat. No. 4,917,900, which is incorporated herein by reference.

Commonly used methods of achieving sustained release are diffusion-controlled release and dissolution-controlled release. In practice, diffusion-controlled release can be produced by formulating the drug in an insoluble matrix. The gastrointestinal fluid penetrate the matrix and the drug diffuses out of the matrix and is adsorbed. When individual drug particles or granules are coated with a slowly soluble coating material such as polyethylene glycol of varying thickness, the time required for dissolution of the coat is proportional to the coating thickness.

Further references which describe the preparation of sustained release drug formulations are Mandal et al., (1996); Abu-Izza et al., (1996); Malley et al., (1996) and Alhaique et al., 1996.

With a sustained release formulation, it is possible to use a single daily dosage, although dividing the desired daily dosage into two or three administrations is preferable.

In accordance with a further embodiment, the invention provides a combination of AZT and an aldehyde oxidase inhibitor, wherein the aldehyde oxidase inhibitor also inhibits metabolism of an additional anti-viral agent given as well as AZT. For example, ketoconazole provides inhibition of AMT formation by aldehyde oxidase and also extends the half-life of protease inhibitors.

Whether administered as separate pharmaceutical compositions or combined in a single dosage form with AZT, aldehyde oxidase inhibitors are prepared for administration by routine techniques of pharmaceutical formulation.

The pharmaceutical compositions of the invention may be administered therapeutically by injection or by oral, nasal, rectal, vaginal or transdermal routes in a variety of formulations, as is known to those in the art. Oral or parenteral routes are preferred.

Formulations of the present invention for oral administration may be in the form of tablets, capsules or powders or in liquid form, as a solution or suspension or emulsion. These formulations may be prepared by conventional techniques, for example as described in Aulton (1988) and Ansel et al. (1995).

Because of the risk of the HIV virus developing resistance to individual anti-retroviral drugs, it is increasingly common to treat HIV infection and AIDS with combinations or cocktails of anti-retroviral drugs.

A high incidence of bone marrow depression has been seen in late stage AIDS, at which time AIDS patients are typically receiving a cocktail of drugs. As seen in Table 6, some drugs used in AIDS therapy, such as dapsone and sulfadiazine, caused accelerated conversion of AZT to AMT by human liver preparations. This suggests that AZT toxicity may actually be increased by the use of some other drugs in combination with AZT. This effect can be reduced by the further inclusion of an aldehyde oxidase inhibitor in the drug cocktail.

The present invention further provides a method for screening candidate compounds and identifying compounds which are potentially useful to reduce or prevent the formation of AMT from AZT in a mammal receiving AZT therapy. Candidate compounds are screened by determining their effect on the formation of AMT from AZT by aldehyde oxidase oxidase. For example, AMT formation in vitro by a preparation of mammalian liver aldehyde oxidase may be examined. A liver cytosolic preparation is preferred. A statistically significant inhibition of the formation of AMT from AZT indicates a suitable compound for further consideration as therapeutic agent for use in combination with AZT in the treatment of HIV infection or AIDS.

A hamster liver cytosolic preparation of aldehyde oxidase is one suitable preparation for carrying out the screening method of the invention. Other tissues with significant aldehyde oxidase activity may also be employed, Such as rabbit, guinea pig, rat or mouse liver (sugihara et al., 1996). Aldehyde oxidase has also been reported in microorganisms, including mammalian intestinal bacteria (Kitamura et al., 1997) and preparations of such microorganisms may also be useful for the screening method of the invention.

An example of a suitable method for determining the effect of a candidate compound on AMT formation from AZT is described in Example 1.

Aldehyde oxidase activity may also be determined by photometric methods, for example as described in Sugihara et al., 1996; Rashidi et al., 1997 and Kitamura et al., 1983.

EXAMPLES

The examples are described for the purposes of illustration and are not intended to limit the scope of the invention.

Methods of protein and peptide biochemistry and immunology referred to but not explicitly described in this disclosure and examples are reported in the scientific literature and are well known to those skilled in the art.

Example 1
Identification of Aldehyde Oxidase Pathway
Materials and Methods
Materials:

[2-$^{14}$C]-AZT (specific activity 55 mCi/mmol) was purchased from Moravek Biochemical (Brea, Calif.) AZT, AMT, NADPH, 2-OHP (2-hydroxypyrimidine), N-methylnicotinamide and all other drugs tested for their effect on AZT reduction were obtained from Sigma Chemical (St. Louis, Mo.). HIV protease inhibitors were obtained from the following companies: saquinavir (Invirase) from Hoffman-La Roche, UK & USA; indinavir (Crixivan) from Merck Inc, USA; ritonavir (norvir) from Abbott, Canada & USA. Silica gel TLC plates with preadsorbent spotting area were from J. T. Baker (20×20 glass plates with 19 channels, catalog #7010-04, Phillipsburg, N.J.).

Liver Enzyme Preparations.

Human liver samples stored at −70° C. were partially thawed, homogenized 1:1 in 1.15% KCl by Potter-Elvehjem tissue homogenizer, centrifuged at 9000g for 20 min, and the supernatant (S9 fraction) was frozen or was further centrifuged at 100,000 g for 60 min. The microsomal pellet was washed and resuspended in phosphate buffer pH 7.4 and both cytosol and microsome fractions were stored at −70° C. until used. Hamster livers were processed by the same method.

Incubation and Radio-TLC Conditions.

An efficient radio-TLC method was developed for separation, identification and measurement of AZT and AMT in human liver microsomal and cytosolic fractions using channelled silica gel TLC plates. Briefly, use of TLC plates with a preadsorbent spotting area allowed the incubation mixture to be applied directly to the plate and eliminated the extraction step. This reduced the experimental variability and simplified the procedure. The recovery of radioactivity from incubation and radio-TLC analysis was quantitative. The method was as follows.

The 0.5 ml standard incubation mixtures (in duplicate) contained a constant amount of $^{14}$C-AZT (about 360,000 dpm, 10 μM alone or plus unlabelled AZT), 5 mM MgCl$_2$, 5 mM NADPH or 7 mM 2-hydroxypyrimidine (2-OHP), 100 μl microsome or cytosol fractions in 10 mM Tris-HCl buffer pH 7.5. The assay was performed in glass Thunberg tubes and started by the addition of co-factor and immediate connecting to the vacuum system (about 20 mm Hg) for 2 min. Preliminary studies showed that it was necessary to use low oxygen tensions in the incubate to obtain AZT reductase activity. The reaction was terminated by opening the tubes to the air followed by the addition of 100 μl of methanol and centrifugation at 3000 rpm for 5 min to sediment the protein.

Sample aliquots (60 μl) and markers of unlabelled AZT and AMT were applied to the preadsorbent spotting area (loading zone) of the TLC plate that was then developed in a solvent system consisting of chloroform-methanol-water-aqueous ammonia (80-20-2-0.2). The compounds, AZT and AMT, separated well and the band shapes were uniform and well resolved with Rf values of 0.85 and 0.2. The TLC bands were visualized by contacting the plate with the phosphorscreen and radioactivity was quantified by Image Quant (Storm Instrument, Molecular Dynamics, California). Control incubations were performed in the absence of either co-factor or enzyme. AMT formation was expressed as the radioactivity in the AMT region as a percentage of the total radioactivity in the AMT and AZT regions (% AMT formed).

AMT Formation by Liver Microsomes and Cytosol

Table 1 shows AMT formation by human liver microsomes and by a cytosolic fraction, in the presence of NADPH which is a cofactor required for microsomal aldehyde oxidase activity, or in the presence of 2-hydroxypyrimidine (2-OHP) which is a specific cofactor required for cytosolic aldehyde oxidase.

As seen in Table 1, the liver cytosolic fraction showed no NADPH-dependent AMT formation and the microsomal fraction showed no 2-OHP-dependent AMT formation. NADPH-dependent AMT formation occurred in the microsomal fraction and a higher level of AMT formation, dependent on 2-OHP, was found in the cytosolic fraction.

Examination of AMT formation in the presence of NADPH or 2-OHP by liver fraction S9 (9000×g supernatant) which contains both microsomes and cytosolic proteins showed that NADPH-dependent or microsomal AMT formation accounted for about 10% of total AMT formation, and 2-OHP-dependent or cytosolic formation for about 90% (data not shown).

AMT formation by a human liver S9 fraction was compared with that by a hamster liver S9 fraction, as the hamster has the highest documented level of liver aldehyde oxidase activity (Kitamura, 1984; by Sugihara, 1996). The hamster liver fraction had greater activity than the human fraction in the presence of either co-factor. The results are shown in Table 2.

Example 2
Screening of Inhibitors of Aldehyde Oxidase-Mediated AMT Formation
Inhibition Studies:

Incubation conditions and radio-TLC assay were as described in Example 1, except for addition of inhibitors. Inhibitors were normally dissolved in buffer or an organic solvent and added in a small volume (10 μl) to the incubation mixture. Inhibitor concentrations in the range of 0.1–2.0 mM were employed.

The results of inhibition studies using human liver cytosolic fraction and either an aldehyde oxidase inhibitor or a xanthine oxidase inhibitor are shown in Table 3. Both aldehyde oxidase and xanthine oxidase are molybdenum-containing enzymes. The absence of inhibition of AMT formation in the presence of allopurinol indicates that xanthine oxidase is not involved in the conversion of AZT to AMT. The aldehyde oxidase inhibitors examined all produced inhibition of AMT formation.

Table 4 shows the results of inhibitor studies using the S9 fraction (microsomes and cytosol) of hamster liver. Both chloramphenicol and ketoconazole gave potent inhibition of AMT formation.

Example 3
Inhibitors of Aldehyde Oxidase-Mediated AMT Formation

A number of compounds were screened for inhibition of AMT formation by human liver, using the methods described in Example 2. The S9 fraction (microsomes and cytosol) of human liver was used.

The results are shown in Table 5, for all compounds showing 20% or greater inhibition.

Antibiotics and vitamins inhibited 2-OHP dependent aldehyde oxidase-mediated AMT formation.

The present invention is not limited to the features of the embodiments described herein, but includes all variations and modifications within the scope of the claims.

REFERENCES

Abu-Izza, K., Garcia-Contreras, L., Lu DR. (1996), Journal of Pharmaceutical Sciences, 85(6):572–6.
Alhaique, F., Santucci, E. Carafa, M., Coviello, T. Murtas, E., Riccieri, F. M., (1996), Biomaterials. 17(20):1981–6.
Ansel et al., (1955), "Pharmaceutical Dosage Forms and Drug Delivery Systems", Sixth Edition, Williams & Wilkins.
Aulton, M. (1988), Ed., "Pharmaceutics: The Science of Dosage Form Design", Churchill Livingstone.
Beedam, C., (1985), Drug Metabolism Reviews, v. 16, pp. 119–156.
Cretton, E. M. et al. (1992), Molecular Pharm., v. 39, pp. 258–266.
Eagling, V. A. (1994), Biochem. Pharmacol., v. 48, pp. 267–276.
Hart, S. et al., (1995), Zentral blatt Veterninarmedizin, 42, 397–409.
Horzinek, M. C. (1987), in 'Viral Infections of Carnivores', Chapter 33, SF 780.4, Elsevir-Appel, v. 58, pp. 337–338.
Kitamura, S., Tatsumi, K., (1983), Chem Pharm Bull. 31:3334–3337.
Kitamura, S., (1984), Biochem. Biophys, Res. Comm., v. 121, pp. 749–754.
Kitamura, S., Sugihara, K. and Tatsumi, K. (1997), J. Pharm. Pharmacol., 49, 253–256.
Malley D. S., Barone, R., Heimemann, M. H., (1996), American Journal of Ophthalmology, 122(5):731–2.
Mandal, T. K., Lopez-Anaya, A., Onyebueke, E., Shekleton, M. (1996), Journal of Microencapsulation. 13(3):257–67.
Rashidi, M. R. Smith, J. A., Clarke, S. E., Beedham, C., (1997), Drug Metab Disp. 25:805–813.
Stagg, M. P. et al. (1992), Clin. Pharmacol. Ther., v. 51, pp. 668–676.
Sugihara, K., (1996), Drug Metab. Disp., v. 24, pp. 199–202.
Veal, G. J. and Back, D., (1995), Gen. Pharmac., v. 26, pp. 1469–1475.

TABLE 1

Comparison of AMT formation by microsomal and cytosolic fractions of human liver

| Cofactor | AMT formation (% AMT formed/0.1 g liver) | |
| --- | --- | --- |
| | Microsomal | Cytosolic |
| NADPH (5 mM) | 3.7% | 0% |
| 2-OHP (7 mM) | 0% | 12.3% |

TABLE 2

Comparison of AMT formation by NADPH and 2-OPH dependent enzymes in S9 fraction of human (H.L.) and hamster (HM) liver

| Cofactor | AMT formation (% AMT formed/0.05 g liver) | | |
| --- | --- | --- | --- |
| | H.L. | H.L. | HM |
| NADPH (5 mM) | 1.8% | 1.5% | 11.9% |
| 2-OHP (7 mM) | 19.6% | 13.8% | 52.3% |
| Ratio (2-OHP/NADPH) | 11 | 9.5 | 4.4 |

TABLE 3

Inhibition of AMT formation in cytosolic fraction of human liver.

| | Relative activity* remaining % control | % Inhibition of control AMT formation |
| --- | --- | --- |
| Control** (no inhibitor) | 100 | 0 |
| Allopurinol (2 mM) | 112 | 0 (X.O.I.) |
| Dicumarol (2 mM) | 22 | 78% (A.O.I.) |
| Menadione (2 mM) | 60 | 40% (A.O.I.) |
| Quercetin (2 mM) | 38 | 62% (A.O.I.) |

*Enzyme activity expressed as % AMT formed
**Control activity: 16.1% AMT formed/0.1 g liver
X.O.I.: xanthine oxidase inhibitor
A.O.I.: aldeyde oxidase inhibitor

TABLE 4

Inhibition of AMT formation in S9 fraction of hamster liver.

| | Relative activity* remaining % control | % Inhibition of control AMT formation |
| --- | --- | --- |
| Control** (no inhibitor) | 100 | 0 |
| Chloramphenicol (1 mM) | 1 | 99 |
| Ketoconazole (1 mM) | 1 | 99 |

*Enzyme activity expressed as % AMT formed
**Control: 30.4% AMT formed/0.015 g liver

TABLE 5

Inhibitors of AMT formation in S9 fraction of human liver

| Inhibitor (1 mM) | % Inhibition* |
| --- | --- |
| Pyrazinamide | 21 |
| Terfenadine | 23 |
| Estradiol | 24 |

TABLE 5-continued

Inhibitors of AMT formation in S9 fraction of human liver

| Inhibitor (1 mM) | % Inhibition* |
|---|---|
| Tinidazole | 28 |
| Nifedipine | 28 |
| Loratadine | 37 |
| Folic acid | 38 |
| Riboflavin | 38 |
| Astemizole | 40 |
| Saquinavir | 43 |
| Indinavir | 53 |
| Thioctic acid | 59 |
| Chloramphenicol | 65 |
| Clarithromycin | 70 |
| Miconazole | 73 |
| Ketoconazole | 73 |
| Pyridoxal | 77 |
| Esculetin | 79 |
| Clotrimazole | 94 |
| Ritonavir | 97 |

*% Inhibition of control AMT formation

TABLE 6

Activation of AMT formation in S9 fraction of human liver

| Activator | % Control Activity |
|---|---|
| Primaquine (1 mM) | 121 |
| Phenylbutazone (1 mM) | 120 |
| Sulfadiazine (1 mM) | 113 |
| Dapsone (1 mM) | 112 |
| Control | 100 |

We claim:

1. A method for screening a candidate compound for potential utility for reducing or preventing the formation of 3'-amino-3'-deoxythymidine (AMT) from 3'-amino-3'-deoxythymidine (AZT) in a mammal receiving AZT therapy comprising the steps of
   (a) providing a candidate compound; and
   (b) determining the effect of the compound on the formation of AMT from AZT by an aldehyde oxidase preparation, an inhibitory effect on the formation of AMT being indicative of said potential utility.

2. The method of claim 1 wherein the aldehyde oxidase preparation is a mammalian aldehyde oxidase preparation.

3. The method of claim 2 wherein the mammalian aldehyde oxidase preparation is a liver aldehyde oxidase preparation.

4. The method of claim 3 wherein the liver aldehyde oxidase preparation is a liver cytosolic fraction from a mammal.

5. The method of claim 4 wherein the effect of the compound on AMT formation is determined by radio-thin layer chromatography.

6. A method for treating HIV infection or AIDS in a mammal comprising administering to the mammal an effective amount of AZT in combination with at least one aldehyde oxidase inhibitor, the aldehyde oxidaze inhibitor being administered in an amount effective to reduce or prevent the formation of AMT from the AZT in the mammal.

7. The method of claim 6 wherein the aldehyde oxidase inhibitor is selected from the group consisting of pyrazinamide, terfenadine, estradiol, tinidazole, nifedipine, loratadine, folic acid, riboflavin, astemizole, saquinavir, indinavir, thioctic acid, chloramphenicol, clarithromycin, miconazole, ketoconazole, pyridoxal, esculetin, clotrimazole and ritonavir.

8. A method for protecting a subject receiving treatment with AZT against toxicity due to AMT comprising administering to the subject receiving treatment with AZT a pharmaceutically acceptable aldehyde oxidase inhibitor in an amount effective to reduce or prevent the formation of AMT.

9. A pharmaceutical composition comprising at least one pharmaceutically acceptable aldehyde oxidase inhibitor, AZT or a pharmaceutically acceptable salt thereof and, optionally, a pharmaceutically acceptable carrier.

10. The composition of claim 9 wherein the aldehyde oxidase inhibitor is selected from the group consisting of pyrazinamide, terfenadine, estradiol, tinidazole, nifedipine, loratadine, folic acid, riboflavin, astemizole, saquinavir, indinavir, thioctic acid, chloramphenicol, clarithromycin, miconazole, ketoconazole, pyridoxal, esculetin, clotrimazole and ritonavir.

11. The method of claim 4 wherein the mammal is selected from the group consisting of hamsters, rabbits, guinea pigs, rats and mice.

12. The method of claim 6 wherein the mammal is a human.

13. The method of claim 8 wherein the mammal is a human.

* * * * *